United States Patent [19]

Delente

[11] Patent Number: 5,211,181
[45] Date of Patent: May 18, 1993

[54] APPARATUS AND METHOD FOR COLLECTING HUMAN BREATH SAMPLES

[75] Inventor: Jacques J. Delente, Kensington, Md.

[73] Assignee: Martek Corporation, Columbia, Md.

[21] Appl. No.: 702,022

[22] Filed: May 17, 1991

[51] Int. Cl.$^5$ .............................................. A61B 5/097
[52] U.S. Cl. ...................................... 128/730; 422/84
[58] Field of Search ........................ 128/719, 727–728, 128/730; 73/863.71–863.72, 864.55, 864.63; 422/84

[56] References Cited

U.S. PATENT DOCUMENTS

| | | | |
|---|---|---|---|
| 3,303,840 | 2/1967 | Etzlinger | 128/2 |
| 3,321,976 | 5/1967 | Jones | 73/421.5 |
| 3,426,745 | 2/1969 | Farr | 128/2 |
| 3,544,273 | 12/1970 | McConnaughey | 23/254 |
| 3,613,665 | 10/1971 | Gorsuch | 128/2 R |
| 3,734,692 | 5/1973 | Lucker et al. | 23/254 R |
| 3,777,571 | 12/1973 | Jaeger | 73/421.5 |
| 3,858,573 | 1/1975 | Ryan et al. | 128/2 C |
| 4,248,245 | 2/1981 | Kempin | 128/719 |
| 4,274,425 | 6/1981 | Lutz et al. | 128/719 |
| 4,402,911 | 9/1983 | Walters | 422/102 |
| 4,579,826 | 4/1986 | Bolton et al. | 436/132 |
| 4,624,929 | 11/1986 | Ullman | 436/179 |
| 4,644,807 | 2/1987 | Mar | 73/864.62 |
| 4,900,514 | 2/1990 | Fuller | 422/84 |
| 4,944,918 | 7/1990 | Desai | 422/22 |
| 4,947,861 | 8/1990 | Hamilton | 128/719 |

Primary Examiner—Lee S. Cohen
Assistant Examiner—Kevin Pontius
Attorney, Agent, or Firm—Rothwell, Figg, Ernst & Kurz

[57] ABSTRACT

A simplified, user-friendly method and apparatus for producing and collecting a human breath sample, and particularly alveolar air, for analysis of the constituent components thereof. The invention includes an elongated, hollow container and a breath delivery device for directing a subject's breath into the container. A closure device is provided for accommodating the insertion of the breath delivery device into the container and for substantially sealing the container. The volume of the container is small in comparison to the normal human breath which has the effect of purging the container of the initial breath portion and leaving primarily only the alveolar air.

7 Claims, 3 Drawing Sheets

APPARATUS AND METHOD FOR COLLECTING HUMAN BREATH SAMPLES

BACKGROUND OF THE INVENTION

1. Field of the Invention

This invention relates generally to a method and apparatus for collecting breath samples from humans and, in particular, is directed to an uncomplicated, user-friendly and relatively inexpensive apparatus and method for collecting such breath samples such that they consist primarily of alveolar gas as expelled from the pockets of the lungs.

2. Description of the Prior Art

Certain diagnostic techniques require analysis of the breath of a human subject to determine whether the breath contains a particular chemical compound, such as ethyl alcohol, carbon dioxide or ammonia, or a non-chemical, such as a particular microorganism. Determining the constituent components of the breath is best accomplished by analyzing the alveolar gas, that is the portion of the exhaled breath which is expelled from the air pockets of the lungs. In exhalation, as the lungs contract, breath contained in the mouth, throat and bronchials is necessarily exhaled first, followed by the breath contained in the alveoli of the lungs. Since it is at the alveoli where the exchange of substances between breath and blood ultimately occurs, the concentration of gaseous or vaporous constituents in the alveoli corresponds more closely to the concentration of substances dissolved in the blood. Thus, if a sample of breath is to be analyzed for the presence of constituents which may be present in the blood, the sample of breath analyzed must be at least primarily alveolar gas.

The equipment commonly used for collecting alveolar breath samples consists of bags, valves, syringe and needles and evacuated containers such as used for blood samples. These devices are expensive and complex which makes them very difficult for a patient to use. For example, U.S. Pat. No. 3,734,692 discloses an alveolar breath sampling apparatus utilizing a complicated compartmentalized bag having first and second inflatable regions. A dual channeled delivery port is constructed into the apparatus and communicates with both regions. The breath sample is collected by breathing into the delivery port resulting in the sequential collection in each region. This device is unnecessarily complex and expensive to construct.

In another known arrangement, the alveolar air portion of a person's breath is separated in response to the temperature of the conveyed air. For example, U.S. Pat. No. 4,248,245 discloses a method and device for separating alveolar air which includes conveying the exhaled air through a conduit and continuously monitoring the temperature of the conveyed air. When the variation in measured temperature drops below a threshold value, the air is directed into a measuring chamber. This device is also excessively complex and expensive to manufacture.

In still another prior art arrangement, two separate collection bags are used interconnected by a conduit. For example, in U.S. Pat. No. 3,544,273, a first collection bag and a second collection bag are connected by a T-shaped conduit having one branch formed into a mouth piece. The breath sample is collected by inflating the first bag with the initial breath poriton and filling the second bag with the alveolar air. The second bag is sealed by using a valve structure. The complexity of these devices and resultant difficulty individual users have in operating them has often resulted in less than accurate measurements. In addition, such prior art systems are intimidating to the user and difficult to use in any event and thus are not as widely used as considered medically prudent for early diagnostic purposes.

Thus, there is a great need for an accurate, inexpensive and most importantly user friendly method and apparatus for collecting a human breath sample, primarily the alveolar portion thereof, for the analysis of the constituent components thereof.

SUMMARY OF THE INVENTION

Accordingly, the present invention provides, in one embodiment thereof, an inexpensive and user-friendly method and apparatus for collecting a human breath sample. In a preferred embodiment, the apparatus comprises an elongated, rigid hollow tubular container having an elongated chamber formed therein. One end of the elongated chamber is closed and the opposite end thereof is provided with an inlet portion forming an opening from the exterior to the interior of the chamber. An elongated, hollow delivery device is also provided which is designed to be inserted into the inlet portion of the chamber and to extend to near the closed end thereof for delivering a breath sample from a subject's mouth to the chamber. A closure means is also provided for substantially sealing the chamber after the breath sample has been collected and the delivery device has been removed from the chamber. The closure means is operable in a first position which accommodates the insertion of the delivery device and in a second position which substantially seals the chamber, thereby trapping and sealing the breath sample in the chamber such that the container can be transported to another location for analysis of the breath sample.

The volume of the elongated chamber is substantially smaller than the volume of a breath sample normally expelled by a human subject such that the exhalation of the breath into the chamber through the breath delivery device purges the chamber of the initial portion of the breath and leaves only primarily the alveolar portion of the expelled breath which is expelled later in the exhalation event.

DETAILED DESCRIPTION OF THE PREFERRED EMBODIMENT

Figures 1, 1A:
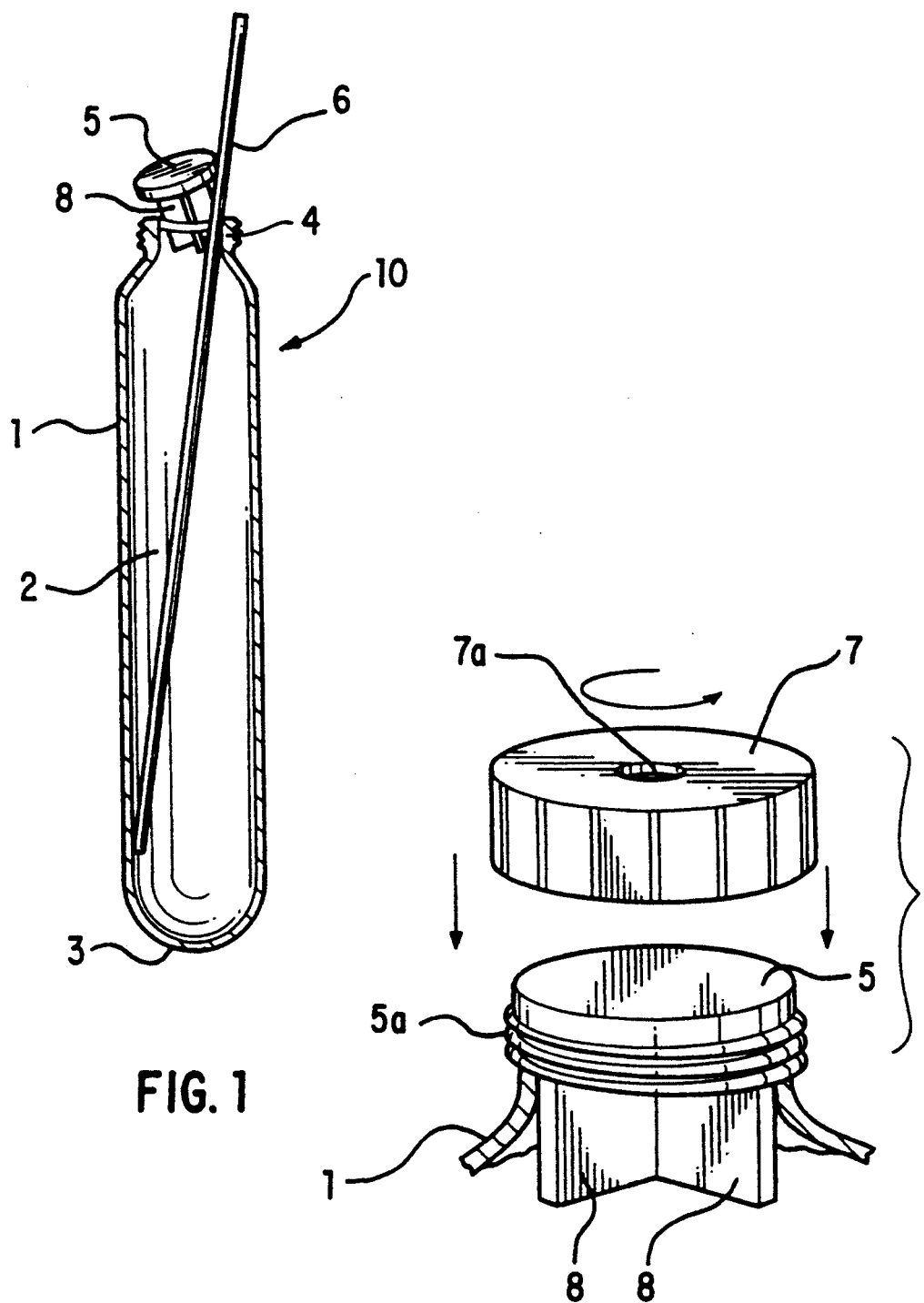
FIG. 1 is a front elevational view of a breath collection apparatus according to a first embodiment of the present invention.
FIG. 1A is an exploded view of a portion of the embodiment of FIG. 1 showing a closure cap means for providing a further seal of the apparatus.

The breath collection apparatus of the present invention will be discussed in detail with reference to FIG. 1 which shows breath collection apparatus 10 including an elongated, hollow, rigid tubular container 1 having an elongated, hollow chamber 2 therein. The elongated container 1 has a closed end 3 and an opposite end thereof having an inlet portion 4 forming an opening to the interior of chamber 2. The elongated tubular container can be any suitable closeable container. In a preferred embodiment, the tubular container is a common commercially available vial or test tube which forms the elongated, hollow chamber 2 which has a length substantially greater than its diameter.

The breath collection apparatus of FIG. 1 further includes an elongated, hollow breath delivery means 6 for delivering a breath sample from a subject's mouth into the chamber 2. The breath delivery means can be any suitable, preferably hollow, device which will facilitate directing a subject's exhaled breath into the container's interior chamber. In a preferred embodiment, the breath delivery means is a common commercially available plastic or glass straw.

The embodiment of FIG. 1 also includes closure means 5 for closing and substantially sealing the inlet portion 4 of the elongated container 1. The closure means 5 operates in at least two different positions. In a first position, the closure means accommodates the insertion of the breath delivery means into the container's interior chamber 2 as is illustrated in FIG. 1. In a second position, the closure means substantially seals the inlet portion 4 of the container 1. In the embodiment shown in FIG. 1, the closure means is placed in the second position to seal the inlet portion 4 after the removal of the delivery means 6.

The closure means 5 is adapted to removably seal the inlet portion of the elongated container 1 and to accommodate the insertion of the delivery means 6 in a manner such that the opening into the chamber 2 is at least partially covered during the use of the delivery means 6. In a preferred embodiment, the closure means 5 is formed of a resilient material, such as butyl rubber, and is shaped in the form of a disk 5 with one or more projecting blades 8 extending therefrom. The blades 8 provide means for facilitating positioning of the closure maens into the first and second positions and for accommodating the insertion of the breath delivery means 6.

In a preferred embodiment as shown in FIG. 1A, a threaded screw cap 7 with a central hole 7a therein is mounted over closure means 5 and in threaded engagement with threads 5a on the tubular container 1 to press the disk 5 against the rim of the tubular container and assure a safe seal. The screw cap 7 is mounted after the closure means has substantially sealed the breath sample in the container 1 and provides a further seal for facilitating storage, moving and shipping of the sealed container. The hole 7a in the cap 7 adapted to permit a sampling needle to be inserted into the sealed breath sample within the chamber 2 to withdraw a portion of the sample without removing the screw cap 7.

The method of collecting a breath sample utilizing the device shown in FIG. 1, according to the present invention, will be described as follows. The individual subject is instructed, preferably by instructions included with the apparatus, to place the closure means in a first position forming an openign at the inlet 4 and to insert the breath delivery means into the container through the opening so formed. The closure means is positioned in such a way that it partially rides over the breath delivery ejmans. The delivery means 6 is preferably inserted such that the end thereof extends well into the chamber 2 and toward the closed end 3 thereof. The subject then exhales one normal breath through the delivery means into the chamber 2. Toward the end of the breath exhalation, the individual pulls the delivery means out of the inlet portion 4 of the container and places the closure means in its second position, substantially sealing the breath sample in the chamber 2.

The volume of elongated container 1 is substantially smaller than the volume of a normal exhaled breath. This comparatively small volume is provided so that as the subject exhales his or her breath through the breath delivery means, the initial portion of the expiration is purged from the interior chamber 2 through the inlet portion 4. Near the end of expiration, substantially only the alveolar air will remain which is then sealed in the container by closure means 5. The screw cap 7 is then screwed on and tightened to provide a further seal.

The elongated container 1 can be of any suitable size which will facilitate purging the initial portion of the expired breath from the container. In a preferred embodiment, the container is a serum bottle or vial made of glass with an inlet portion having a diameter ranging from about 10 mm to about 25 mm and having a total volume ranging from about 5 ml to about 100 ml.

The method and apparatus for collecting a human breath sample according to the present invention have many advantages over the prior art breath collection systems. The breath collection device 10 comprises very few elements and is inexpensive and easily constructed. Most importantly, because device 10 is so uncomplicated and is thus very user-friendly, the ease of use results in fewer user errors and improves the accuracy of the ultimate breath constituent analyses.

Another advantage of the present invention is its amenability to automated analysis. The slotted freeze drying stoppers 5, used in the preferred embodiment, can easily be pierced by a sampling needle, such as for automated injection into a gas isotope ratio mass spectrometer, or a gas chromatograph hydrogen analyzer. As noted above, the central hole 7a in the screw cap 7 allows the sampling needle to operate without having to remove the screw cap. The subject or patient can self administer the sampling without assistance at home as well as in the physician's office. All items are easily and conveniently incorporated in a diagnostic test kit. No syringes or needles (which represent a possible health risk) are required.

Figure 2:
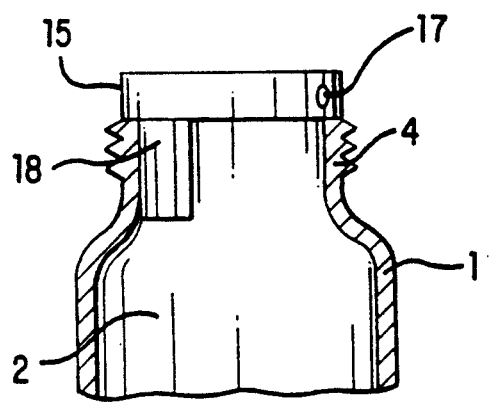
FIG. 2 is a cross-sectional view of the closure means in accordance with a second embodiment of the present invention.
Figure 3:
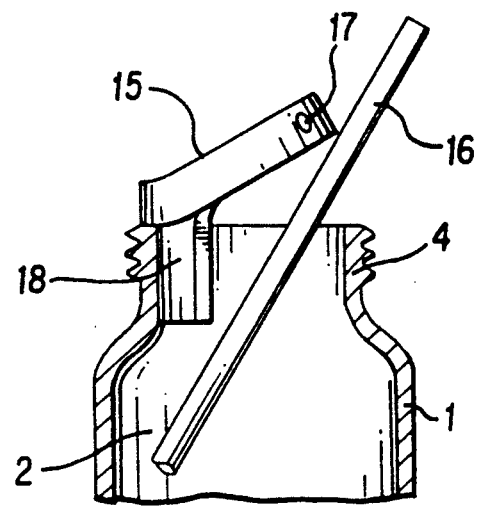
FIG. 3 is a cross-sectional view of the closure means shown in FIG. 2.
Figure 4:
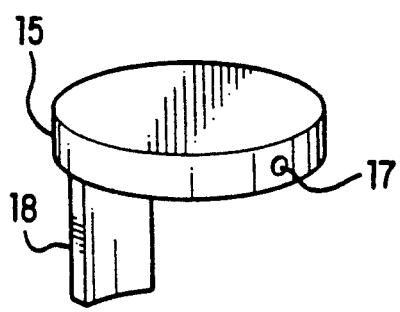
FIG. 4 is an enlarged top elevational view of the closure means shown in FIG. 2.

FIGS. 2-4 illustrate a second embodiment of the present invention. In this embodiment, a disk shaped closure means 15 is formed with a flexible projection 18 (formed, for example, of butyl rubber) which is affixed to the inside of the inlet portion 4 of the elongated container 1. Because the closure means is fixed to the container, handling and operating the breath collection device is greatly facilitated. The possibility of mishandling or losing the closure is essentially eliminated. The projection 18 can be affixed to the container by any suitable means, such as glue. In a preferred embodiment, the projection 18 is lined on one face with PTEE (Kimble Cat.#73816-15) and is glued by putting a very small droplet of Superglue ™ (Cyanoacrylate made by The Loctite Co.) on the rim of the rubber face of the disk, and pressing onto the rim of a Borosilicate glass disposable screw cap culture tube. Closure means 15 is also constructed with a dot or marker, illustrated at 17, which indicates where the device should be lifted for inserting the breath delivery means. The marker is preferably positioned diametrically opposed to the place where the glue is applied.

FIG. 3 illustrates the closure means in the first position which accommodates the insertion of the breath delivery means 16. The individual user can very easily lift the stopper at marker 17 and will proceed to direct the breath sample into the chamber 2 using the breath delivery means. FIG. 2 illustrates the closure means in the second position, substantially sealing the container after the delivery means has been removed.

Figure 4A:
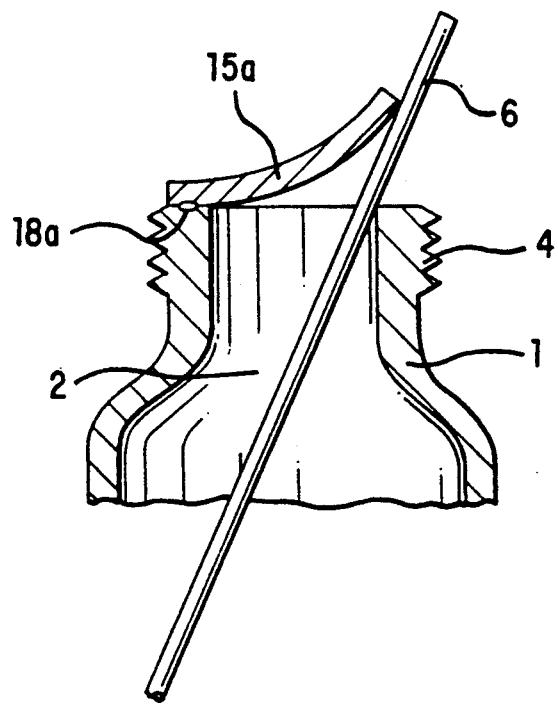
FIG. 4A is a cross-sectional view of a third embodiment of the invention.

In an alternative embodiment, the closure means can be provided without the projection 18 and can be affixed at one location to the rim of the inlet portion of the elongated container. Such an embodiment is shown in FIG. 4A. In this embodiment, a flexible preferably disk shaped closure means 15a is provided which is substantially similar to the portion 15 of the embodiment of FIGS. 2-4. The closure means 15a is secured at a single spot 18a on the periphery thereof to the periphery of the inlet portion 4 of the container 1. The single spot 18a is secured to the inlet portion 4 by a suitable adhesive in the same manner as described in the embodiment of FIGS. 2-4 in connection with the attachment of the projection 18. The flexible closure means 15a is normally flat as is the portion 15 of FIG. 2, and is resiliently urged into sealing engagement with the inlet portion 4 of the container 1. The closure means 15a can be flexed to an open position as shown in FIG. 4A to accommodate the insertion of the delivery means 6.

Figure 5:
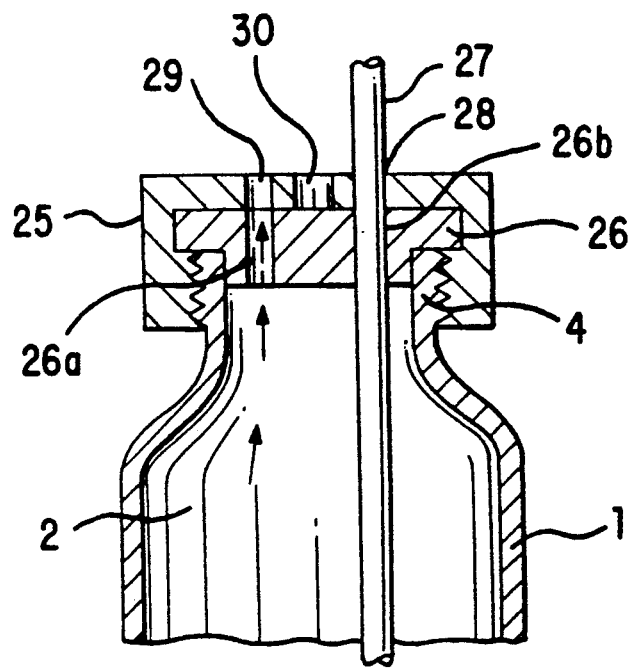
FIG. 5 is a cross-sectional view of a closure means in accordance with a fourth embodiment of the present invention.
Figure 6:
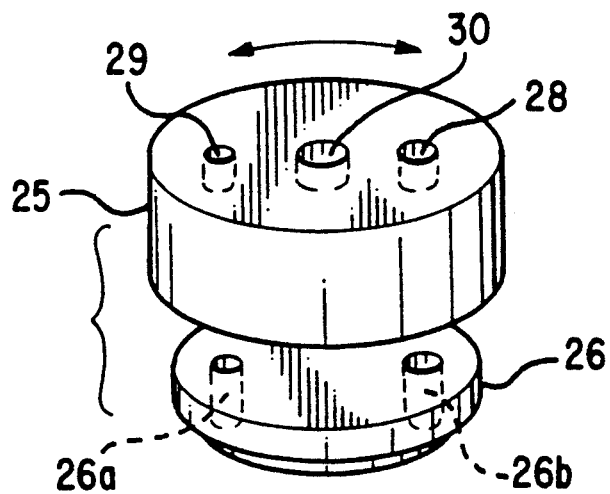
FIG. 6 is an enlarged top elevational view of the closure means shown in FIG. 5.

In still another embodiment of the present invention, FIGS. 5 and 6 illustrate a closure means which further facilitates using the breath collection device. A closure means 26 such as a device described in connection with FIG. 1 is positioned to substantially seal the inlet portion of the elongated container. The closure means has at least a first hole 26a and a second hole 26b formed therethrough which are positioned radially spaced from the center of the closure 26. A cap 25 is rotatably securable to the elongated container in any suitable manner, such as by threaded engagement therewith. Cap 25 has a first hole 28 and a second hole 29 formed therethrough which can be aligned with the first and second holes in the closure means 26 by rotating the cap 25 into a position of alignment, as illustrated in FIG. 5. The cap 25 also has a hole 30 extending therethrough at the center thereof to accommodate the insertion of a sampling needle without the necessity of removing the cap 25 after it has been secured in place in sealing engagement with the inlet portion 4 of the container 1.

The operation of the breath collection device of the embodiment of FIGS. 5 and 6 is as follows. The cap 25 is loosely secured on the inlet portion 4 of the container 1 and the individual subject rotates the cap 25 until the first hole 28 is aligned with the hole 26b in the closure means 26 and the second hole 29 is aligned with the hole 26a in the closure means 26. The respective positioning of the holes is such that these alignments occur at a single selected position of cap 25 relative to the closure means 26. The breath delivery means 27 is then inserted through one of the first or second holes 28 or 29 in cap 25 and into the interior chamber of the elongated container with the delivery means being positioned so that the end thereof extending into the chamber extends to a position near the closed end 3 of the chamber 2. For illustrative purposes, FIG. 5 shows breath delivery means 27 inserted into the first hole 28. The subject then exhales a normal breath through the breath delivery means 17 and into the chamber 2. Because of the small volume of the chamber 2 relative to the volume of a normal expelled human breath from a subject, the initial portion of the expiration will be purged through the second aligned holes 26a and 29 thereby leaving primarily only the alveolar portion of the expiration in the chamber 2. The cap 25 is then rotated so that the first and second holes are moved out of alignment. thereby closing the paths into and out of the chamber 2. The cap 25 is tightened down on the closure means 26 to firmly seal the breath sample inside the chamber 2. FIG. 6 illustrates the alignment of the holes 28 and 29 in the cap 25 with the holes 26b and 26a of the closure means 26.

Although the invention has been described in connection with certain embodiments, it is not limited to them. Modifications within the scope of the following claims will be apparent to those skilled in the art without derogating the scope of applicant's novel contribution to the art.

What is claimed is:

1. A method of producing and collecting a human breath sample for analysis of the constituent components thereof, comprising:
   (a) providing an elongated, rigid hollow tubular container having an elongated chamber therein, one end of said container being closed and an opposite end thereof having an inlet portion forming an opening to the interior of said chamber;
   (b) providing an elongated, hollow breath delivery means for delivering a breath sample from a subject's mouth, said breath delivery means being insertable into said chamber through said inlet portion to deliver to said chamber a breath sample expelled from said subject's mouth, said chamber having a volume which permits collection of only primarily an alveolar portion of the expelled breath;
   (c) providing a closure means for closing and substantially sealing the inlet portion of said tubular container; said closure means being provided with a first position accommodating the insertion of said delivery means and a second position sealing said inlet portion of said chamber;
   (d) positioning said closure means into said first position and inserting one end of said delivery means into the mouth of said subject and an opposite end thereof into said chamber through said inlet portion;
   (e) expelling a breath sample into said breath delivery means based on a normal full exhale volume and permitting a portion of said breath to flow out of said inlet portion of said container; and
   (f) removing said delivery means and positioning said closure means into said second position substantially sealing said inelt portion of said elongated chamber whereby a said breath sample containing a substantial amount of the alveolar portion of the subject's expelled breath is captured in said elongated tubular container.

2. A breath sample collection kit for collecting and storing a human breath sample for analysis of the constituent components thereof, comprising in combination:
   (a) an elongated, rigid hollow tubular container having an elongated chamber therein, one end of said container being closed and an opposite end thereof having an nilet portion forming an opening to the interior of said chamber;

(b) a hollow breath delivery means for delivering a breath sample from a subject's mouth, said breath delivery means being insertable into said chamber through said inlet portion to deliver to said chamber a breath sample expelled from said subject's mouth, said chamber having a volume which is substantially less that the volume of a breath sample normally expelled by a human such that said expulsion of said breath purges said chamber of an initial portion of said breath through said inlet portion leaving only primarily an alveolar portion of the expelled breath; and (c) a closure means for closing and substantially sealing the inlet portion of said tubular container, said closure means being provided with a first position for accommodating the insertion of said delivery means into said chamber, and a second position for sealing said inlet portion of said tubular container.

3. A breath sample collection kit as set forth in claim 2 wherein said closure means is secured in said second position at one edge thereof to said inlet portion, the remaining portion of said closure means not so secured at said one edge being resiliently movable to said first position, thereby providing an access opening to said chamber through said inlet portion and accommodating insertion of said delivery means into said chamber, said closure means being secured in a position to resiliently urge said remaining portion thereof to said second position.

4. An apparatus for collecting a human breath sample for analysis of the constituent components thereof comprising:

(a) an elongated, rigid hollow tubular container having an elongated chamber therein, one end of said container being closed and an pposite end thereof having an inlet portion forming an opening to the interior of said chamber;

(b) a hollow breath delivery means for delivering a breath sample to said elongated chamber from a subject's mouth, said breath delivery means being insertable into said subject's mouth at one end and insertable into said chamber through said inlet portion at an opposite end, said chamber having a volume which is substantially less than the volume of a breath sample normally expelled by a human such that the expulsion of said breath purges said elongated chamber of an initial portion of said breath through said inlet portion collecting only primarily the alveolar portion of the expelled breath; and (c) a closure means for closing and substantially sealing the inlet portion of said tubular container, said closure means having a first position for accommodating the insertion of said breath delivery means into said chamber and a second position for substantially sealing the inlet portion of said tubular container.

5. An apparatus for collecting a human breath sample as set forth in claim 4 wherein said closure means is secured in said second position at one edge thereof to said inlet portion, the remaining portion of said closure means not so secured at said one edge being resiliently movable to said first position, thereby providing an access opening to said chamber through said inlet portion and accommodating insertion of said delivery means into said chamber, said closure means being secured in a position to resiliently urge said remaining portion thereof to said second position.

6. A breath sample collection kit for collecting and storing a human breath sample for analysis of the constituent components thereof, comprising:

(a) an elongated, rigid hollow tubular container having an elongated chamber therein, one end of said container being closed and an pposite end thereof having an inlet portion forming an opening to the interior of said chamber;

(b) a hollow breath delivery means for delivering a breath sample from a subject's mouth, said breath delivery means being insertable into said chamber through said inlet portion to deliver to said chamber a breath sample expelled from said subject's mouth, said chamber having a volume which is substantially less that the volume of a breath sample normally expelled by a human such that said expulsion of said breath purges said chamber of an initial portion of said breath through said inlet portion leaving only primarily an alveolar portion of the expelled breath; and (c) a closure means for closign and substantially sealing the inlet portion of said tubular container, said closure means being provided with a first position for accommodating the insertion of said delivery means such that a portion of said delivery means extends past said closure means into said chamber, and a second position for sealing said inlet portion of said tubular container.

7. An apparatus for collecting a human breath sample for analysis of the constituent components thereof comprising:

(a) an elongated, rigid hollow tubular container having an elongated chamber therein, one end of said container being clsoed and an opposite end thereof having an inlet portion forming an pening to the interior of said chamber;

(b) a hollow breath delivery means for delivering a breath sample to said elongated chamber from a subject's mouth, said breath delivery means being insertable into said subject's mouth at one end and insertable into said chamber through said inlet portion at an opposite end, said chamber having a volume which is substantially less than the volume of a breath sample normally expelled by a human such that the expulsion of said breath purges said elongated chamber of an initial portion of said breath through said inlet portion collecting only primarily the alveolar portion of the expelled breath; and (c) a closure means for closing and substantially sealing the inlet portion fo said tubular container, said closure means having a first position for accommodating the insertion of said breath delivery means such that a portion of said delivery means extends past said closure means into said chamber and a second position for substantially sealing the inlet portion of said tubular container.

* * * * *

UNITED STATES PATENT AND TRADEMARK OFFICE
CERTIFICATE OF CORRECTION

PATENT NO. : 5,211,181
DATED      : May 18, 1993
INVENTOR(S): Jacques J. Delente It is certified that error appears in the above-identified patent and that said Letters Patent is hereby corrected as shown below:

Col. 1, line 42, "compartm.entalized" should be --compartmentalized--.

Col. 7, line 2, "nilet" should be --inlet--.

Col. 8, line 12, "pposite" should be --opposite--.

Col. 8, line 41, "clsoed" should be --closed--.

Col. 8, line 42, "pening" should be --opening--.

Col. 8, line 58, "fo" should be --of--.

Signed and Sealed this

Twenty-ninth Day of March, 1994

Attest:

BRUCE LEHMAN

Attesting Officer     Commissioner of Patents and Trademarks